United States Patent [19]

Rosen

[11] Patent Number: 5,082,442
[45] Date of Patent: Jan. 21, 1992

[54] DENTAL CROWN ANALOG FOR ORTHODONTIC ANCHORAGE

[76] Inventor: David B. Rosen, 9 Trodden Path, Lexington, Mass. 02173

[21] Appl. No.: 723,745

[22] Filed: Jul. 1, 1991

[51] Int. Cl.⁵ ............................ A61C 3/00; A61C 8/00; A61C 5/08
[52] U.S. Cl. ........................................ 433/17; 433/24; 433/173; 433/218
[58] Field of Search .................. 433/17, 202.1, 218, 433/173, 174, 2, 22, 24

[56] References Cited

U.S. PATENT DOCUMENTS

| | | | |
|---|---|---|---|
| 851,578 | 4/1907 | West | 433/191 |
| 853,984 | 5/1907 | Lauderdale | 433/218 |
| 3,866,321 | 2/1975 | Valen | 433/174 |
| 4,447,210 | 5/1984 | Hidaka et al. | 433/173 |
| 4,522,596 | 6/1985 | Ashkinazy | 433/173 |
| 4,738,062 | 4/1988 | Dickey | 433/173 |
| 4,744,756 | 5/1988 | Ross | 433/173 |
| 4,850,870 | 7/1989 | Lazzara et al. | 433/174 |
| 4,988,292 | 1/1991 | Rosen | 433/8 |
| 4,988,298 | 1/1991 | Lazzara et al. | 433/173 |

*Primary Examiner*—John J. Wilson
*Assistant Examiner*—Cindy A. Cherichetti
*Attorney, Agent, or Firm*—Alfred H. Rosen

[57] ABSTRACT

A dental crown analog for anchoring an orthodontic archwire to a dental implant fixture installed in a patient who is edentulous at the site where such anchorage is desired has a hollow tubular passage integral with the analog and extending mesially-distally through the analog close to an adjacent buccal or lingual surface. This passage has a slot-shaped opening at one end, the larger dimension of which is generally parallel to the adjacent surface, and the larger dimension tapers toward a smaller generally cylindrical cross-section between its ends or at the other end. Where the smaller cross section is between the ends of the passage the other end of the passage also has a slot-shaped opening. A tube for holding the archwire may be fitted in the passage, rockably mounted in the smaller portion of the passage.

20 Claims, 1 Drawing Sheet

DENTAL CROWN ANALOG FOR ORTHODONTIC ANCHORAGE

This invention relates in general to the dental field of orthodontics, and more particularly to a dental crown analog for orthodontic anchorage to a dental implant fixture in a patient who is edentulous at the site where such anchorage is desired. This invention is related to the invention of my U.S. Pat. No. 4,988,242, and to the invention of my copending application for U.S. Pat. Ser. No. 07/400,881 filed August 30, 1989, the disclosures of which are incorporated herein by reference.

BACKGROUND OF THE INVENTION

In one class of systems used in orthodontic practice archwires cooperating with brackets affixed to buccal or lingual surfaces of teeth are used to adjust the relative positions of teeth in a dental arch with appropriate forces applied over time to individual teeth in the arch. These wires are anchored at their ends to tubes and the like affixed to the patient's molars, pre-molars, or other suitable teeth. In cases of patients who have lost their molars or premolars, or otherwise lack suitable anchorage, the use of molar tubes and the like has not been available to orthodontists. Recent developments in the art of dental implantology now provide a variety of artificial root fixtures, notably the endosseous implant fixture, which provide an opportunity to fill that need for the partially edentulous patient. The inventions of my above-referenced patent and pending application introduce a new system and pre-fabricated components which facilitate orthodontic anchorage to a dental implant fixture installed at an edentulous site. My present invention further improves dental crown analogs intended for use in my new system.

GENERAL NATURE OF THE INVENTION

A dental implant fixture in the class of endosseous implant fixtures consists essentially of an elongated body implanted in the patient's jawbone and having an elongated socket for receiving a fitting or fittings which fix a prosthodontic restoration on the implant fixture. Commonly, the socket is an internally-threaded receiving bore, and the restoration is fixed to the implanted fixture with a bolt threaded into that bore. Other forms of dental implants are in use, and a wide variety of material are used to make them. This invention is disclosed in connection with the endosseous implant fixture as currently known to be in use, as a best mode now known to practice the invention. It will be understood that the invention is not limited to the details of the illustrative disclosure; to the contrary, the invention is intended for use with any and all substitutes for natural tooth structures that are capable of providing the required anchorage, whether presently known or made available in the future.

Control of dental plaque, consisting of bacteria, is a very important factor in the general health of the soft and hard tissue which supports the teeth. If bacterial plaque is allowed to accumulate in the gingival sulcus it will result in gingival inflammation and bone loss in the affected areas. This becomes particularly important during the process of orthodontic therapy. The mechanical brackets, bands and other attachments heretofore used by orthodontists to affix molar tubes and the like to teeth serve as plaque-retentive areas that require extra effort on the part of the patient in order to keep them clean and prevent periodontal disease.

Orthodontic therapy typically takes 1-2 years, during which time it is imperative to maintain the highest level of oral hygiene. My present invention incorporates a design that is characterized by smooth buccal and lingual surfaces, in order to minimize plaque retention.

During the process of orthodontic therapy there is a constant process of remodeling of the bone surrounding the teeth being moved. Bone is resorbed on the pressure side of the teeth being moved and bone is deposited on the tension side of the same teeth. Bacterial plaque can interfere with this process. The presence of inflammation, which is in response to the bacterial deposits, inhibits the process of bony deposition during tooth movement. This results in a tooth being moved and bone being resorbed on the pressure side with no simultaneous repair at the site being vacated by the tooth. When a dental implant is involved this accumulation of bacterial plaque can result in loss of osseointegration and a subsequent loosening and failure of the implant-a disastrous result. It is an object of this invention to provide an environment that is easily cleaned by the patient during the process of orthodontic therapy and to minimize the accumulation of bacterial plaque.

Generally according to the invention a standardized prefabricated dental crown analog, designed and intended as a component for dental implant systems, provides orthodontic anchorage for archwires and the like. In its most general form the invention provides a prefabricated dental crown analog incorporating an orthodontic wire anchor consisting essentially of a hollow tubular passage integral with said crown analog and extending mesially-distally through the analog closer to an adjacent exterior buccal or lingual surface than to the center of the analog, the passage having a substantially slot-shaped opening at one end the larger dimension of which opening extends generally parallel to the adjacent exterior surface, the larger dimension diminishing progressively along the passage toward the other end of the passage, which may have a cylindrical cross-section. Alternatively, the anchor passage may have slot-shaped openings at both ends the larger dimensions of which diminish progressively toward a mid-point in the passage, where the passage may again have a cylindrical, or nearly cylindrical cross-section. In preferred embodiments of the invention, tubes for engaging an archwire are rockably fitted into each anchor passage. For purposes of attachment to an endosseous dental implant fixture crown analogs according to the invention may comprise features disclosed in my above-mentioned patent and copending application, including for example a tubular passage extending medially through the analog from its occlusal end to its gingival end and having near the gingival end an internal flange providing a shoulder for the head of a bolt by which to attach the crown analog to an endosseous implant fixture having an internally-threaded receiving bore, together with means to fix the crown analog in a rotational position around the axis of the bore. This invention is disclosed in fuller detail with reference to the accompanying drawing illustrating embodiments of it, in which:

DETAILED DESCRIPTION OF THE DRAWINGS

Figure 1:
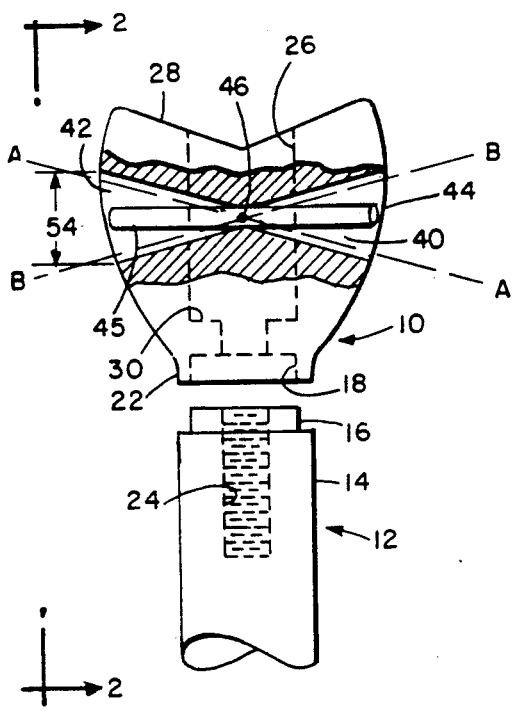
FIG. 1 is a side view, partly broken away, of a first embodiment of the invention.
Figure 2:
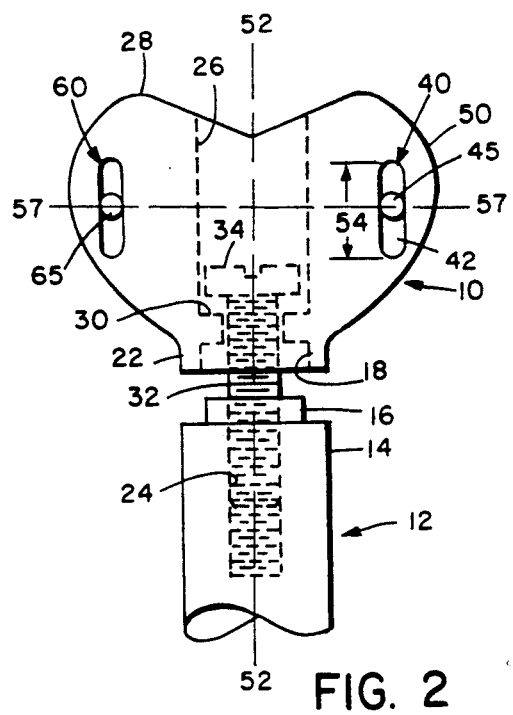
FIG. 2 is a view on line 2—2 of FIG. 1.

In FIGS. 1 and 2 a dental crown analog 10 is shown with an endosseous dental implant fixture 12 to which the analog is adapted to be attached. The fixture 12 has at its gingival end 14 a projecting anti-rotation fitting 16 of a well-known type, for example one having a hexagonal cross-section. The analog has at its gingival end 22 a corresponding anti-rotation socket 18 which in use is fitted over the fitting 16. The implant fixture 12 includes an axially-oriented internally-threaded bore 24. The crown analog 10 includes an axially-oriented bore 26 extending from its gingival end 22 to its occlusal end 28. An internal flange 30 in the analog bore 26 provides a shoulder for the head 34 of a bolt 32 by which to attach the crown analog 10 to the implant fixture 12.

As seen in FIG. 1, the crown analog 10 incorporates an integral passage 40 which extends mesially-distally through the body of the analog. This passage has a cross-section which is slot-shaped at its ends 42, 44, and cylindrical at its mid-point 46. As seen in FIG. 2, the integral passage 40 is closer to an adjacent exterior buccal or lingual surface 50 than to the center-line 52—52 of the analog, and the larger dimension 54 of the slot-shaped opening 42 is generally parallel to the adjacent exterior surface 50. Referring again to FIG. 1, the larger dimension 54 of the passage 40 diminishes progressively along said passage toward the mid-point 46. The other end 44 of the passage 40 is similar; the passage is symmetrical about its mid-point 46, giving the appearance of a double-fan-shaped passage having two fanshaped portions meeting at their respective apices. As seen in FIG. 2, the crown analog may have a second similar passage 60 adjacent the remaining exterior buccal or lingual surface. The analog illustrated in FIG. 2 may be a molar; its shape is contoured so that preferably the buccal and lingual surfaces bulge outwardly as compared with the contour of a natural molar so that the passages 40 and 60 will be more nearly in the same locations as would molar tubes attached to a natural tooth, the more readily to receive an archwire (not shown). A tube 45, 65, respectively, is rockably fitted into each of the passages 40, 60, respectively. Each of these tubes is fitted preferably snugly so as the be retained by friction in the cylindrical midsection of its passage 40,60 so that it can be rocked around an axis 57,57, which is generally perpendicular to the adjacent buccal or lingual surface, as is shown in FIG. 2, between the directions A—A and B—B, shown in FIG. 1. In use, the crown analog 10 is fixed on an installed endosseous implant fixture and locked in a desired orientation around the center-line 52—52, and an archwire (not shown) is anchored in one of the tubes 45 or 65 in one of the double-fan-shaped passages 40 or 60. The archwire can thus pass through this passage 40 or 60 in any direction ranging from the direction A—A to the direction B—B shown in FIG. 1, while being held and guided by the tube 45 or 65 that is enclosed in that passage. The tubes 45 and 65 thus serve the purpose of a molar tube, with the additional function that they are orientable around the transverse axis 57—57. In practice, the dental practitioner can fill the fanshaped spaces around the tube with an acrylic or other suitable material, to provide smooth exterior surfaces for the above-mentioned hygienic reasons as well as to stabilize the tube in its chosen orientation.

Figure 3:
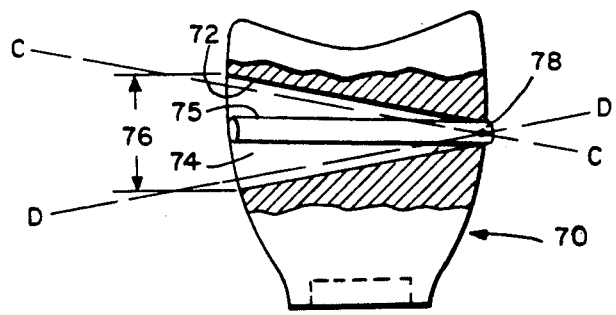
FIG. 3 is a side view, partly broken away, of a second embodiment of the invention.

The embodiment of the invention illustrated in FIG. 3 is a crown analog 70 characterized by a single-fan-shape anchor passage 72, in which there is only one wide end 74 having a slot-shaped entrance with a larger dimension 76, and including a tube 75 rockably anchored in its narrow end 78. The narrow end 78 of this passage has a substantially cylindrical cross-section. The larger dimension 76 gradually diminishes from the wide end 74 to the narrow end 78. An archwire can pass through the tube 75 in this passage 72 in any direction ranging from the direction C—C to the direction D—D.

It is contemplated that a crown analog according to the invention can be used without a tube 45, 65 or 75 in the passage 40, 60 or 72, respectively. Embodiments of the invention including such tubes are preferred.

I claim:

1. A prefabricated dental crown analog having an exterior size and contour to approximate the dimensions and shape of a natural tooth and an orthodontic wire anchor consisting essentially of hollow tubular means providing an integral passage extending mesially-distally through said analog closer to an adjacent exterior buccal or lingual surface than to the center thereof, characterized in that said passage has a substantially slot-shaped opening at one end the larger dimension of which extends generally parallel to said adjacent surface, said larger dimension diminishing progressively along said passage toward the other end of said passage.

2. A dental crown analog according to claim 1 in which said larger dimension diminishes progressively along the entire length of said passage to said other end.

3. A dental crown analog according to claim 1 in which said passage has a substantially slot-shaped opening at each of its ends and the larger dimension of each opening diminishes progressively along said passage toward an intermediate region in said passage.

4. A dental crown analog according to claim 3 in which said passage has a substantially cylindrical cross-section in said intermediate region.

5. A dental crown analog according to claim 1 including a tube in said passage, said tube having one end accessible through said slot-shaped opening, said tube being held in said passage in a region remote from said slot-shaped opening.

6. A dental crown analog according to claim 5 in which said tube is rockable in said region around an axis that is generally perpendicular to said adjacent surface.

7. A dental crown analog according to claim 3 including a tube in said passage, said tube being held in said intermediate region and having its ends accessible respectively through said slot-shaped openings.

8. A dental crown analog according to claim 7 in which said tube is rockable in said intermediate region around an axis that is generally perpendicular to said adjacent surface.

9. A dental crown analog according to claim 2 including a tube in said passage, said tube being held at one end in said other end of said passage, the other end of said tube being accessible via said slot-shaped opening.

10. A dental crown analog according to claim 9 in which said tube is rockable in said passage around an axis through said other end of said passage that is generally perpendicular to said adjacent surface.

11. A dental crown analog according to claim 1 in which said adjacent surface bulges outwardly as compared with the contour of said natural tooth to locate said passage in substantially the same location that a molar tube affixed to said natural tooth would occupy.

12. A dental crown analog according to claim 1 including means at its gingival end to affix said analog to a dental implant fixture.

13. A dental crown analog according to claim 12 including means to fix the orientation of said analog around an axis that runs through said analog from the occlusal surface thereof to said gingival end.

14. A dental crown analog according to claim 6 including means at its gingival end to affix said analog to a dental implant fixture.

15. A dental crown analog according to claim 14 including means to fix the orientation of said analog around a second axis that runs through said analog from the occlusal surface thereof to said gingival end, said second axis being substantially perpendicular to said first-named axis.

16. A dental crown analog according to claim 8 including means at its gingival end to affix said analog to a dental implant fixture.

17. A dental crown analog according to claim 16 including means to fix the orientation of said analog around a second axis that runs through said analog from the occlusal surface thereof to said gingival end, said second axis being substantially perpendicular to said first-named axis.

18. A dental crown analog according to claim 10 including means at its gingival end to affix said analog to a dental implant fixture.

19. A dental crown analog according to claim 18 including means to fix the orientation of said analog around a second axis that runs through said analog from the occlusal surface thereof to said gingival end, said second axis being substantially perpendicular to said first-named axis.

20. A hygienically improved dental crown analog for orthodontic anchorage comprising a prefabricated dental crown analog incorporating an integral passage extending mesially-distally through said analog closer to an adjacent exterior buccal or lingual surface than to the center thereof, tubular means in said passage for receiving an orthodontic archwire, and means to adjust said tubular means around an axis that is generally perpendicular to said surface.

* * * * *